(12) United States Patent
Sun et al.

(10) Patent No.: US 11,904,301 B2
(45) Date of Patent: Feb. 20, 2024

(54) FLUORINE REMOVAL FROM ANTIMONY FLUOROHALIDE CATALYST USING CHLOROCARBONS

(71) Applicant: THE CHEMOURS COMPANY FC, LLC, Wilmington, DE (US)

(72) Inventors: Xuehui Sun, Kennett Square, PA (US); Mario Joseph Nappa, Leesburg, FL (US); Karl Krause, Kennett Square, PA (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 590 days.

(21) Appl. No.: 17/273,342

(22) PCT Filed: Sep. 6, 2019

(86) PCT No.: PCT/US2019/049889
§ 371 (c)(1),
(2) Date: Mar. 4, 2021

(87) PCT Pub. No.: WO2020/051417
PCT Pub. Date: Mar. 12, 2020

(65) Prior Publication Data
US 2021/0316282 A1    Oct. 14, 2021

Related U.S. Application Data

(60) Provisional application No. 62/728,392, filed on Sep. 7, 2018.

(51) Int. Cl.
| | | |
|---|---|---|
| *B01J 27/32* | (2006.01) | |
| *B01J 27/10* | (2006.01) | |
| *C01G 30/00* | (2006.01) | |

(52) U.S. Cl.
CPC .............. *B01J 27/32* (2013.01); *B01J 27/10* (2013.01); *C01G 30/007* (2013.01)

(58) Field of Classification Search
CPC . B01J 27/32; B01J 27/10; B01J 27/12; C01G 30/007
USPC ..................... 502/35, 36, 224, 353
See application file for complete search history.

(56) References Cited

U.S. PATENT DOCUMENTS

| | | | | |
|---|---|---|---|---|
| 4,438,088 A | * | 3/1984 | Weaver | C07C 17/208 570/154 |
| 4,851,595 A | * | 7/1989 | Gumprecht | C07C 17/208 570/170 |
| 5,155,082 A | | 10/1992 | Tung et al. | |
| 6,034,016 A | * | 3/2000 | Boyce | B01J 38/42 502/227 |
| 2010/0331583 A1 | * | 12/2010 | Johnson | C07C 17/206 570/166 |
| 2015/0152028 A1 | | 6/2015 | Johnson et al. | |
| 2016/0311736 A1 | * | 10/2016 | Lu | B01J 23/83 |
| 2017/0283348 A1 | * | 10/2017 | Wang | C07C 17/25 |
| 2018/0127338 A1 | | 5/2018 | Sun et al. | |
| 2018/0370878 A1 | | 12/2018 | Andre et al. | |

FOREIGN PATENT DOCUMENTS

| | | | | | |
|---|---|---|---|---|---|
| CN | 102199071 A | * | 9/2011 | ............. | C07C 17/35 |
| CN | 107635955 A | * | 1/2018 | ............. | B01J 23/16 |
| EP | 2080748 A2 | * | 7/2009 | ........... | C07C 17/087 |
| GB | 1113998 A | | 5/1968 | | |
| WO | 2017103378 A1 | | 6/2017 | | |

OTHER PUBLICATIONS

Ronan M. Bellabarba, "Catalysts for modern fluorinated refrigerants." Journal of Fluorine Chemistry 244, pp. 1-18. (Year: 2021).*
Heng-Dao Quan et al., "Preparation of 1,1,1,3,3-pentafluoropropane (HFC-245fa) by using a SbF5-attached catalyst." Journal of Fluorine Chemistry 128, pp. 190-195. (Year: 2007).*

* cited by examiner

*Primary Examiner* — Patricia L. Hailey
(74) *Attorney, Agent, or Firm* — McNees Wallace & Nurick LLC

(57) ABSTRACT

A method of chlorinating a antimony fluorohalide catalyst is disclosed. In one embodiment the method comprises contacting an antimony fluorohalide catalyst that contains one or more fluorines with a regenerating agent chosen from 2-chloro-3,3,3-trifluoropropene (1233xf), 1,1,1,3-tetrachloropropane (250fb), 2-chloro-1,1,1,2-tetrafluoropropane (HCFC-244bb) and combinations of 1233xf, 250fb, and 244bb, under conditions effective to exchange at least one fluorine in the antimony fluorohalide catalyst with chlorine. The method can be used to regenerate spent antimony fluorohalide catalyst, for example regenerating $SbCl_5$ from $SbF_5$.

18 Claims, No Drawings

FLUORINE REMOVAL FROM ANTIMONY FLUOROHALIDE CATALYST USING CHLOROCARBONS

CROSS-REFERENCES TO RELATED APPLICATIONS

This application is a National Stage Entry of PCT/US2019/049889, filed Sep. 6, 2019, which claims the benefit of U.S. Provisional Application No. 62/728,392, filed Sep. 7, 2018, which is incorporated by reference herein in its entirety.

FIELD OF THE INVENTION

The present invention is directed generally to the removal of fluorine from antimony fluorohalide catalysts, which catalysts are employed, for example, in the synthesis of halogenated materials such as 2-chloro-1,1,1,2-tetrafluoropropane (HCFC-244bb) used in the manufacture of 2,3,3,3-tetrafluoropropene (HFO-1234yf).

BACKGROUND OF THE INVENTION

Hydrofluoroolefins (HFOs), such as tetrafluoropropenes, including 2,3,3,3-tetrafluoropropene (HFO-1234yf), are known to be effective refrigerants, heat transfer media, propellants, foaming agents, blowing agents, gaseous dielectrics, sterilant carriers, polymerization media, particulate removal fluids, carrier fluids, buffing abrasive agents, displacement drying agents, and power cycle working fluids. Unlike chlorofluorocarbons (CFCs) and hydrochlorofluorocarbons (HCFCs), both of which potentially damage the Earth's ozone layer, HFOs do not contain chlorine and thus pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf are among the materials being developed for use in many of the aforementioned applications.

One process to make HFO-1234yf employs 1,1,2,3-tetrachloropropene (1230xa, or TCP) as starting raw material. The process comprises the following three steps:

Step (1): 1230xa+3HF→2-chloro-3,3,3,-trifluoropropene (1233xf)+3HCl in a vapor phase reactor charged with a solid catalyst;

Step (2): 1233xf+HF→2-chloro-1,1,1,2-tetrafluoropropane (HCFC-244bb) in a liquid phase reactor charged with a liquid catalyst; and Step (3): 244bb→1234yf+HCl in a vapor phase reactor.

An alternative process to make HFO-1234yf employs 1,2-dichloro-3,3,3,-trifluoropropane (243db) as starting raw material. The process comprises the following three steps:

Step (1): 243db→1233xf+HCl in the vapor phase (with catalyst) or liquid phase (with base and optional catalyst).

Step (2): 1233xf+HF→2-chloro-1,1,1,2-tetrafluoropropane (HCFC-244bb) in a liquid phase reactor charged with a soluble catalyst; and Step (3): 244bb→1234yf+HCl in a vapor phase reactor.

Typically, $SbCl_5$ is charged to the reactor in Step (2). $SbCl_3$ may also be charged to the reactor, either separately or premixed with the $SbCl_5$. The $SbCl_5$ can also be produced in situ by charging the $SbCl_3$ and reacting some or all of the $SbCl_3$ with $Cl_2$. While not intending to be bound or limited, it is believed that the active catalyst in this Step (2) is an antimony fluoride catalyst, such as having the formula $SbF_nCl_{5-n}$, where n>0 and n<5. Antimony catalyst recovered from this reaction is typically highly fluorinated—for example, the recovered catalyst may include compounds such as $SbF_5$, $SbF_4Cl$, and/or $SbF_3Cl_2$. Techniques to reduce or remove the fluorine from recovered antimony catalyst so the catalyst can be reused have been explored. These include reacting recovered antimony catalyst with agents such as carbon tetrachloride ($CCl_4$) or chloroform ($CHCl_3$) to exchange fluorine for chlorine. However, the use of $CCl_4$ produces contaminants such as $CCl_3F/CCl_2F_2$ (F11/F12), whereas the use of $CHCl_3$ produces contaminants such as $CHFCl_2/CHClF_2$ (F21/F22). These contaminants are themselves waste, and create additional problems of disposal with associated increases in cost. There is thus a need for an improved method to remove fluorine from antimony catalyst containing fluorine that minimizes or eliminates production of contaminants and reduces cost.

SUMMARY OF THE INVENTION

In one aspect of the invention, the disclosure provides a method of chlorinating an antimony fluorohalide catalyst. The method comprises contacting an antimony fluorohalide catalyst that contains one or more fluorines with a regenerating agent, the regenerating agent being chosen from 2-chloro-3,3,3-trifluoropropene (1233xf), 1,1,1,3-tetrachloropropane (250fb), 2-chloro-1,1,1,2-tetrafluoropropane (244bb) and combinations of 1233xf, 250fb and 244bb, under conditions effective to exchange at least one fluorine in the antimony catalyst with chlorine in the regenerating agent. Beneficially, insofar as 1233xf is feed material in the manufacture of 244bb, the product of this chlorinating treatment when the regenerating agent is 1233xf is 244bb and/or 1234yf, either of which is a desirable product. Likewise, co-products in the use of 250fb as a regenerating agent include 3-chloro-1,1,1-trifluoropropane (253fb) and/or 2-chloro-1,1,1,3-tetrafluoropropane (1242zf), both of which are useful intermediates in the manufacture of 1234yf or 3,3,3-trifluoropropene (1243zf). Hence, rather than generating contaminant waste products necessitating additional disposal and related costs, valuable materials are produced and the operation is simplified.

Another aspect of the invention comprises the foregoing method wherein the regenerating agent comprises 1233xf.

Another aspect of the invention comprises the foregoing method wherein the regenerating agent comprises 250fb.

Another aspect of the invention comprises the foregoing method wherein the regenerating agent comprises 244bb.

Another aspect of the invention comprises the foregoing method wherein the antimony fluorohalide catalyst comprises at least one of (i) $SbF_nX_{5-n}$, wherein n is an integer of 1 to 5, and X is a halogen other than fluorine; or (ii) as $SbF_mX'_{3-m}$, wherein m is an integer of 1 to 3, and X' is a halogen other than fluorine; or mixtures of (i) and (ii).

Another aspect of the invention comprises the foregoing method wherein the antimony fluorohalide catalyst comprises $SbF_nX_{5-n}$, wherein n is an integer of 1 to 5, and X is chlorine and the product is a chlorine-containing catalyst.

Another aspect of the invention comprises the foregoing method wherein the antimony fluorohalide catalyst comprises $SbF_mX'_{3-m}$, wherein m is an integer of 1 to 3, and X' is chlorine.

Another aspect of the invention comprises the foregoing method wherein the antimony fluorohalide catalyst comprises $SbF_3$.

Another aspect of the invention comprises the foregoing method wherein the antimony fluorohalide catalyst comprises $SbF_nX_{5-n}$, wherein n is an integer of 1 to 5, and X is chlorine and $SbF_mX'_{3-m}$, wherein m is an integer of 1 to 3, and X' is chlorine.

Another aspect of the invention comprises the foregoing method wherein the antimony fluorohalide catalyst comprises $SbF_5$, $SbF_4Cl$, $SbF_3Cl_2$, or mixtures thereof.

Another aspect of the invention comprises the foregoing method wherein the antimony fluorohalide catalyst comprises $SbF_4Cl$ and $SbF_3Cl_2$.

Another aspect of the invention comprises the foregoing method wherein the chlorine-containing antimony catalyst resulting from the exchange comprises $SbCl_5$.

Another aspect of the invention comprises the foregoing method wherein the chlorine-containing antimony catalyst resulting from the exchange comprises $SbCl_3$.

Another aspect of the invention comprises the foregoing method wherein the contacting occurs at a temperature between about 80° C. and about 120° C.

Another aspect of the invention comprises the foregoing method wherein the molar ratio of the regenerating agent to the antimony fluorohalide catalyst to the agent is between about 1 to about 5.

In one aspect of the invention, the disclosure provides a method of regenerating and recovering a spent antimony fluorohalide catalyst comprising:
(a) treating a spent antimony fluorohalide catalyst to produce a chlorinated antimony catalyst comprising
  (i) $SbF_nX_{5-n}$, wherein n is an integer of 1 to 5, and X is a halogen other than fluorine, or
  (ii) as $SbF_mX'_{3-m}$, wherein m is an integer of 1 to 3, and X' is a halogen other than fluorine, or mixtures of (i) and (ii),
with a regenerating agent chosen from 2-chloro-3,3,3-trifluoropropene (1233xf), 1,1,1,3-tetrachloropropane (250fb), 2-chloro-1,1,1,2-tetrafluoropropane (244bb) and combinations of two or more of 1233xf, 250fb and 244bb, under conditions effective to produce a chlorinated antimony catalyst from the spent antimony fluorohalide catalyst; and
(b) recovering the chlorinated antimony catalyst.

Another aspect of the invention comprises the foregoing method wherein the chlorinated antimony catalyst comprises $SbCl_5$.

Another aspect of the invention comprises the foregoing method wherein the chlorinated antimony catalyst comprises $SbCl_3$.

Another aspect of the invention comprises the foregoing method wherein the contacting occurs at a temperature between about 80° C. and about 120° C.; and the molar ratio of the regenerating agent to the spent antimony is between about 1 to about 5.

In one aspect of the invention, the disclosure provides a method to prepare 2-chloro-1,1,1,2-tetrafluoropropane (244bb) comprising contacting 2-chloro-3,3,3,-trifluoropropene (1233xf) with HF and a chlorinated antimony catalyst under conditions effective to produce a composition that comprises 244bb, wherein the chlorinated antimony catalyst is prepared by treating a spent antimony fluorohalide catalyst comprising
$Sb_{Fn}X_{5-n}$, wherein n is an integer of 1 to 5, and X is a halogen other than fluorine, or
as $Sb_{Fm}X'_{3-m}$, wherein m is an integer of 1 to 3, and X' is a halogen other than fluorine, or mixtures of (i) and (ii), with a regenerating agent chosen from 2-chloro-3,3,3-trifluoropropene (1233xf), 1,1,1,3-tetrachloropropane (250fb), 2-chloro-1,1,1,2-tetrafluoropropane (244bb) and combinations of two or more of 1233xf, 250fb and 244bb, under conditions effective to produce the chlorinated antimony catalyst from the spent antimony fluorohalide catalyst.

Another aspect of the invention comprises the foregoing method wherein the chlorinated antimony catalyst comprises $SbCl_3$ or $SbCl_5$.

Another aspect of the invention comprises the foregoing method wherein the chlorinated antimony catalyst comprises $SbCl_3$ and at least one of $SbFCl_2$ or $SbF_2Cl$.

Another aspect of the invention comprises the foregoing method wherein the chlorinated antimony catalyst comprises $SbCl_5$ and at least one of $SbFCl_4$, $SbF_2Cl_3$, $SbF_3Cl_2$, or $SbF_4Cl$.

In one aspect of the invention, the disclosure provides a method to prepare 2,3,3,3-tetrafluoropropene (1234yf) comprising:
providing a starting composition comprising at least one compound having the structure of Formula III:

$$CX''_3-CHCl-CH_2X'' \qquad \text{(Formula III)}$$

wherein each X'' is independently selected from F, Cl, Br and I, provided that at least one of X'' is not F;
dehydrohalogenating said starting composition under conditions effective to produce a first intermediate composition comprising 2-chloro-3,3,3-trifluoropropene (1233xf);
contacting said first intermediate composition comprising 1233xf with HF and a chlorinated antimony catalyst under conditions effective to produce a second intermediate composition comprising 244bb; and
dehydrochlorinating at least a portion of said 244bb to produce a reaction product comprising 1234yf, wherein the chlorinated antimony catalyst is prepared by treating a spent antimony fluorohalide catalyst comprising $SbF_nX_{5-n}$, wherein n is an integer of 1 to 5, and X is a halogen other than fluorine, or
as $SbF_nX'_{3-m}$, wherein m is an integer of 1 to 3, and X' is a halogen other than fluorine, or mixtures of (i) and (ii),
with a regenerating agent chosen from 2-chloro-3,3,3-trifluoropropene (1233xf), 1,1,1,3-tetrachloropropane (250fb), 2-chloro-1,1,1,2-tetrafluoropropane (HCFC-244bb) and combinations of two or more of 1233xf, 250fb and 244bb, under conditions effective to produce the chlorinated antimony catalyst from the spent antimony fluorohalide catalyst.

Another aspect of the invention comprises the foregoing method wherein the starting composition comprises 1,2-dichloro-3,3,3,-trifluoropropane (243db).

Another aspect of the invention comprises the foregoing method wherein the chlorinated antimony catalyst comprises $SbCl_3$ or $SbCl_5$.

Another aspect of the invention comprises the foregoing method wherein the chlorinated antimony catalyst comprises $SbCl_3$ and at least one of $SbFCl_2$ or $SbF_2Cl$.

Another aspect of the invention comprises the foregoing method wherein the chlorinated antimony catalyst comprises $SbCl_5$ and at least one of $SbFCl_4$, $SbF_2Cl_3$, $SbF_3Cl_2$, or $SbF_4Cl$.

In one aspect of the invention, the disclosure provides a composition comprising at least one antimony fluorohalide catalyst selected from the group consisting of
(i) $SbF_nX_{5-n}$m wherein n is an integer of 1 to 5, and X is a halogen other than fluorine, and
(ii) as $SbF_mX'_{3-m}$, wherein m is an integer of 1 to 3, and X' is a halogen other than fluorine, or mixtures of (i)

and (ii); and at least one member selected from the group consisting of 2-chloro-3,3,3-trifluoropropene (1233xf), 1,1,1,3-tetrachloropropane (250fb), 2-chloro-1,1,1,2-tetrafluoropropane (HCFC-244bb) and combinations of two or more of 1233xf, 250fb and 244bb.

Other features and advantages of the present invention will be apparent from the following more detailed description, taken in conjunction with the accompanying drawings which illustrate, by way of example, the principles of the invention.

DETAILED DESCRIPTION OF THE INVENTION

The foregoing general description and the following detailed description are exemplary only and are not restrictive of the invention as defined in the claims herein. Other features and benefits of any one or more embodiments will be apparent following the detailed description and the claims.

For purposes herein, an antimony fluorohalide catalyst is a composition comprising $SbF_nX_{5-n}$ and/or $SbF_mX'_{3-m}$, wherein n>0 and n≤5, m>0 and m≤3, and each X and each X' are independently halogens other than fluorine. Both $SbF_nX_{5-n}$, and $SbF_mX'_{3-m}$ may be present in the antimony fluorohalide catalyst. In a certain embodiment, the antimony fluorohalide catalyst consists of $SbF_nX_{5-n}$. In another embodiment, the antimony fluorohalide catalyst consists of $SbF_mX'_{3-m}$. The antimony fluorohalide catalyst may be spent antimony catalyst recovered from a process adding HF to an olefin such as 1233xf as illustrated above.

The antimony fluorohalide catalyst may be a component of a reaction mixture which further comprises one or more of organics, HF, hydrolyzed and oxidized antimony species.

For purposes herein, the product of treating the antimony fluorohalide catalyst may be referred to as simply an antimony catalyst or an antimony halide catalyst. The antimony catalyst is a composition comprising $SbF_{n'}X_{5-n'}$ and/or $SbF_{m'}X'_{3-m'}$, wherein n'>0 and n'<5, m'>0 and m'<3, and each X and each X' are independently halogens other than fluorine, provided n'<n and m'<m. Both $SbF_{n'}X_{5-n'}$ and $SbF_{m'}X'_{3-m'}$ may be present in the antimony fluorohalide catalyst. In a certain embodiment, the antimony fluorohalide catalyst consists of $SbF_{n'}X_{5-n'}$. In another embodiment, the antimony fluorohalide catalyst consists of $SbF_{m'}X'_{3-m'}$.

In one embodiment, the disclosure relates to a method of chlorinating an antimony fluorohalide catalyst that comprises contacting an antimony fluorohalide catalyst that contains one or more fluorines with a regenerating agent chosen from 2-chloro-3,3,3-trifluoropropene (1233xf), 1,1,1,3-tetrachloropropane (250fb), 2-chloro-1,1,1,2-tetrafluoropropane (244bb) and combinations of 1233xf, 250fb and 244bb, under conditions effective to exchange at least one fluorine in the antimony catalyst with chlorine. Fluorine in the antimony catalyst can be exchanged from one to completely exchanged. The antimony fluorohalide catalyst may be antimony (V), antimony (III), and mixtures thereof. In one practice, the antimony fluorohalide catalyst comprises an antimony (V) fluorohalide catalyst having the formula (i) $SbF_nX_{5-n}$, wherein n>0 and n<5, and X is a halogen other than fluorine, e.g. chlorine. Without limitation, an example of an antimony fluorohalide catalyst of formula (i) is $SbF_5$. The antimony fluorohalide catalyst may also comprise a mixture of two or more of $SbFX_4$, $SbF_2X_3$, $SbF_3X_2$, $SbF_4X$ and $SbF_5$. In the practice of this aspect of the disclosure, the result of the contacting is an exchange of at least one fluorine in the antimony fluorohalide catalyst with chlorine. Thus, for example, when an antimony fluorohalide catalyst of formula (i) is $SbF_5$, the exchange results in the chlorine-containing catalyst $SbClF_4$, $SbCl_2F_3$, $SbCl_3F_2$, $SbCl_4F$, and/or the fully chlorinated catalyst $SbCl_5$.

In another practice, the antimony fluorohalide catalyst comprises an antimony (III) fluorohalide catalyst having the formula (ii) $SbF_mX'_{3-m}$, wherein m>0 and m<3, and X' is a halogen other than fluorine, e.g. chlorine; in another practice the antimony fluorohalide catalyst is a mixture of (i) and (ii). Without limitation, an example of an antimony fluorohalide catalyst of formula (ii) is $SbF_3$. The antimony fluorohalide catalyst may also comprise a mixture of two or more of $SbFX_2$, $SbF_2X$ and $SbF_3$. The result of the contacting is an exchange of at least one fluorine in the antimony fluorohalide catalyst with chlorine. Thus, for example, when an antimony fluorohalide catalyst of formula (ii) is $SbF_3$, the exchange results in the chlorine-containing catalyst $SbClF_2$, $SbCl_2F$, and/or the fully chlorinated catalyst $SbCl_3$.

The conditions effective for treating a antimony fluorohalide catalyst with a regenerating agent include forming a reaction mixture of the antimony fluorohalide catalyst and the regenerating agent, contacting the reaction mixture at a temperature of between about 80° C. and about 120° C.; and between about 110° C. and about 100° C., e.g. about 105° C. In one embodiment, the total molar ratio of regenerating agent, e.g., 1233xf, to antimony (i.e. 1233xf/Sb) is about 0.5 to about 20.0; and about 1 to about 10; and about 1 to about 5. Without limitation, the regenerating agent, e.g., 1233xf, can be fed at ratios lower than herein described, but for a longer period of time until the total amount fed is at a ratio of greater than 1. In one practice, the molar ratio is about 1:1. The regenerating agent, e.g. 1233xf, is at least 2% pure; and in other practices can be about 10% to about 100% pure, for example about 95% pure. The contacting of the regenerating agent can be achieved by means known in the art, including pre-mixing it with the antimony fluorohalide catalyst that contains one or more fluorines; or adding it prior to, or after the introduction of the antimony fluorohalide catalyst that contains one or more fluorines into a reaction vessel, which reaction vessel can be heated at the temperatures described herein, and which can be comprised of suitable materials of construction, such as low alloy steel, high alloy steel, nickel alloy carbon steel, SS304, SS316, AL6XN, Inconel® 600, Inconel® 625, Incoloy® 800, Incoloy® 825, Monel® 400, Hastelloy® C-276, and Alloy 20; or vessels lined with corrosive resistant materials such as PTFE, PFA, and the like.

Agitation by means known in the art may be optionally employed. The contact time is sufficient to enable an exchange of at least one fluorine for a chlorine and includes, without limitation, contact for about 2 hours to about 7 days; including about 2 hours to 2 days, and including about 3 hours to about 24 hours at the temperatures herein described; contact times can be shorter with recirculation and/or reflux of the regenerating agent. In one practice, contact is at a temperature of about 105° C. and a mole ratio of about 1:1, and a contact time of at least 12 hours is employed. In another practice, after sufficient contact, the reaction mixture is cooled down to ambient or other temperatures lower than contact temperature, e.g. about 20° C. to about 60° C., using means known in the art.

Another embodiment of the disclosure relates to a method of regenerating and recovering a spent antimony fluorohalide catalyst to produce a chlorinated antimony catalyst, the method comprising (a) treating a spent antimony fluorohalide catalyst with a regenerating agent chosen from 2-chloro-3,3,3-trifluoropropene (1233xf), 1,1,1,3-tetrachloropropane (250fb), 2-chloro-1,1,1,2-tetrafluoropropane (244bb) and combinations of two or more of 1233xf, 250fb and 244bb, under conditions effective to produce a fully chlorinated antimony catalyst (n' or m' equals 0), or a substantially fully chlorinated antimony catalyst (n' or m' is greater than 0 and less than 1), from the spent antimony fluorohalide catalyst; and (b) recovering the fully chlorinated antimony catalyst ($SbCl_5$ for spent antimony catalyst (i), and $SbCl_3$ for spent antimony catalyst (ii), or alternatively substantially fully chlorinated antimony catalyst, $SbF_{n'}Cl_{5-n'}$, or $SbF_{m'}Cl_{3-m'}$, where n' or m' is less than n or m, respectively. Conditions effective are as described herein and include, for example, contacting at a temperature between about 80° C. and about 120° C., at a molar ratio of regenerating agent to spent antimony (e.g., 1233xf/Sb) of about 0.5 to about 20; and about 1 to about 10, and about 1 to about 5. The chlorinated antimony catalyst may be recovered by means known in the art.

In various non-limiting practices of the disclosure: (1) when the regenerating agent is or comprises 1233xf, the contacting of the antimony fluorohalide catalyst with the regenerating agent occurs in the absence of and/or in the presence of trace amounts of any other reactants, such as, without limitation, 245fb, 244bb, HCl, HF, and other chlorofluorocarbons; (2) when the regenerating agent is or comprises 245fb, the contacting of the antimony fluorohalide catalyst with the regenerating agent occurs in the absence of and/or in the presence of trace amounts of any other reactants, such as, without limitation, 1233xf, 244bb, HCl, HF, and other chlorofluorocarbons; (3) when the regenerating agent is or comprises 244bb, the contacting of the antimony fluorohalide catalyst with the regenerating agent occurs in the absence of and/or in the presence of trace amounts of any other reactants, such as, without limitation, 1233xf, 245fb, HCl, HF, and other chlorofluorocarbons.

In another embodiment, the regenerating agent consists essentially of 1233xf; in another embodiment, the regenerating agent consists of 1233xf. In another embodiment, the regenerating agent consists essentially of 250fb; in another embodiment, the regenerating agent consists of 250fb. In another embodiment, the regenerating agent consists essentially of 244bb; in another embodiment, the regenerating agent consists of 244bb. In another embodiment, the regenerating agent consists essentially of a combination of 1233xf and 250fb; in another embodiment, the regenerating agent consists of a combination of 1233xf and 250fb. In another embodiment, the regenerating agent consists essentially of a combination of 1233xf, 250fb and 244bb; in another embodiment, the regenerating agent consists of a combination of 1233xf, 250fb and 244bb. In another embodiment, the regenerating agent consists essentially of a combination of 1233xf and 244bb; in another embodiment, the regenerating agent consists of a combination of 1233xf and 244bb. In another embodiment, the regenerating agent consists essentially of a combination of 244bb and 250fb; in another embodiment, the regenerating agent consists of a combination of 244bb and 250fb.

In one embodiment, this disclosure provides a process to treat a process stream comprising a spent antimony fluorohalide catalyst with a regenerating agent. The process stream comprises a spent antimony fluorohalide catalyst and may further comprise halogenated organic compounds. The halogenated organic compounds may include, for example, hydrochlorofluorocarbons, hydrofluorocarbons, hydrochlorocarbons and fluorochlorocarbons. Particular examples include 2-chloro-1,1,1,2-tetrafluoropropane (244bb), 2-chloro-3,3,3,-trifluoropropene (1233xf), among others.

The process stream may further comprise hydrolyzed and/or oxidized antimony species. The process stream may further comprise HCl and/or HF. The process stream may further comprise any two or more of halogenated organic compounds, hydrolyzed antimony species, oxidized antimony species, HCl and HF.

In another embodiment, the disclosure relates to a process to prepare 2-chloro-1,1,1,2-tetrafluoropropane (244bb) comprising contacting 2-chloro-3,3,3,-trifluoropropene (1233xf) with HF and a chlorinated antimony catalyst under conditions effective to produce a composition that comprises 244bb, wherein the chlorinated antimony catalyst is or comprises a catalyst prepared by treating an antimony fluorohalide catalyst with a regenerating agent chosen from 2-chloro-3,3,3-trifluoropropene (1233xf), 1,1,1,3-tetrachloropropane (250fb), 2-chloro-1,1,1,2-tetrafluoropropane (244bb) or combinations of two or more of 1233xf, 250fb and 244bb, under conditions effective to produce the chlorinated antimony catalyst from the antimony fluorohalide catalyst. This process may be performed in gas phase or liquid phase reactors, preferably liquid phase. The process may be performed in one or more reactors, including without limitation, Continuous Stirred Tank Reactor (CSTR) or multi-stage CSTR, comprised of materials suitable for a fluorination reaction. Preferably, a reactor is constructed in relevant part from materials resistant to the corrosive effects of hydrogen fluoride (HF) and catalyst, such materials including e.g. Hastelloy®, Inconel®, Monel®. A reactor may otherwise be lined with PTFE or PFA as known in the art. Preferably, the process is performed at about 70° C. to about 120° C. and about 50 to about 120 psig.

In another embodiment, the disclosure relates to a process to prepare 2,3,3,3-tetrafluoropropene (1234yf). In one practice, the process to prepare 1234yf comprises the following steps: (a) providing a starting composition comprising at least one compound having a structure selected from Formula I, II and II:

$$CX''_2\!=\!CCl\!-\!CH_2X'' \qquad \text{(Formula I)}$$

$$CX''_3\!-\!CCl\!=\!CH_2 \qquad \text{(Formula II)}$$

$$CX''_3\!-\!CHCl\!-\!CH_2X'' \qquad \text{(Formula III)}$$

wherein each X" is independently selected from F, Cl, Br and I, provided that at least one of X" is not F; (b) when the starting composition comprises a compound having the structure of Formula I, contacting the starting composition with HF in a reaction zone under conditions effective to produce a first intermediate composition comprising 2-chloro-3,3,3-trifluoropropene (1233xf); (c) contacting said first intermediate composition comprising 1233xf with HF in the presence of an antimony halide catalyst under conditions effective to produce a second intermediate composition comprising 244bb; and (d) dehydrochlorinating at least a portion of said 244bb to produce a reaction product comprising 1234yf, wherein the antimony halide catalyst is prepared by treating an antimony fluorohalide catalyst comprising (i) $SbF_nX_{5-n}$, wherein n>0 and n<5, and X is a halogen other than fluorine, or (ii) as $SbF_mX'_{3-m}$, wherein n>0 and n<3, and X' is a halogen other than fluorine, or mixtures of (i) and (ii), with a regenerating agent chosen from 2-chloro-3,3,3-trifluoropropene (1233xf), 1,1,1,3-tetrachloropropane (250fb), 2-chloro-1,1,1,2-tetrafluoropropane (244bb), and combinations of two or more of 1233xf, 250fb and 244bb, under conditions effective to produce the chlorinated antimony catalyst from the antimony fluorohalide catalyst. The chlorinated antimony catalyst so produced can be recovered by means known in the art and employed in step (2) of the foregoing process to make 1234yf. As to various practices for Steps (1)-(3) in this process to prepare 1234yf, without limitation, the intermediate compositions produced in each step may or may not be purified before use in the next step. In some embodiments, the purification of the compositions may include distillation, nitrogen purging, and/or vacuum distillation.

In one embodiment of Step (a): a starting composition which includes a compound having Formula (I), e.g., 1,1,2,3-tetrachloropropene (TCP), reacts with anhydrous HF in a first vapor phase reactor (fluorination reactor) to produce a mixture of 2-chloro-3,3,3-trifluoropropene (1233xf) and HCl. The reaction may be performed in the presence of a catalyst, such as a fluorinated chromium oxide. The reaction may be conducted in a first vapor phase reactor, such as at a reaction temperature of about 200° C. to about 400° C. and a reaction pressure of about 0 to about 200 psig. The effluent stream exiting the vapor phase reactor may optionally comprise additional components, such as un-reacted HF, heavy intermediates, and HFC-245cb. In case of a vapor phase process, the reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

In one embodiment, a starting composition, which includes a compound having Formula (III), e.g., 1,2-dichloro-3,3,3-tetrafluoropropane (243db), is dehydrohalogenated to produce a product mixture containing 2-chloro-3,3,3-trifluoropropene (1233xf). The dehydrohalogenation reaction is a dehydrochlorination reaction when the starting composition comprises 243db. The dehydrochlorination reaction is performed in a reaction zone and may occur in the vapor phase with a catalyst or in liquid phase with base. For example, WO 2012/115934 discloses vapor phase reaction of 243db with a carbon catalyst. WO 2012/115938 discloses vapor phase reaction of 243db with a chromium oxyfluoride catalyst. WO 2017/044719 discloses reaction of 243db with a fluorinated alkane in the presence of a fluorination catalyst to produce 1233xf, as well as other compounds useful for producing 1234yf. WO 2017/044724 discloses liquid phase reaction of 243db with caustic. Other methods may be used when starting with a compound having Formula (III) as will be known to those skilled in the art.

In Step (2): an antimony catalyst produced by the method described in the present disclosure is employed whereby 1233xf, produced in Step (1), is converted, such as to more than about 95% of 244bb in one or more reaction zones. Thus, in one practice, Step (2) involves contacting the first intermediate composition comprising 1233xf with HF in the presence of an antimony catalyst produced by the method of the present disclosure, under conditions effective to produce a second intermediate composition comprising 244bb.

In Step (3): the second intermediate composition comprising 244bb produced from Step (2) is fed to a second vapor phase reactor (dehydrochlorination reactor) to be dehydrochlorinated to make the desired product 2,3,3,3-tetrafluoropropene (1234yf). In one practice, this dehydrochlorination can be performed thermally, in the absence of a catalyst, at temperatures of about 400° C. or greater. In another practice, the vapor phase reactor contains a catalyst that can catalytically dehydro chlorinate 244bb to make 1234yf. The catalysts in this regard may be metal halides, halogenated metal oxides, neutral (or zero oxidation state) metal or metal alloy, or activated carbon in bulk or supported form. When metal halides or metal oxides catalysts are used, preferred are mono-, bi-, and tri-valent metal halides, oxide and their mixtures/combinations, and more preferred are mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments may include any of those known in the prior art, particularly those that employ HF, $F_2$, HCl, $Cl_2$, HBr, $Br_2$, HI, and $I_2$ as the halogenation source. When neutral, i.e., zero valent, metals, metal alloys and their mixtures are used, useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel® 400, Inconel® 825, Inconel® 600, and Inconel® 625. Preferred catalysts include activated carbon, stainless steel (e.g. SS 316), austenitic nickel-based alloys (e.g. Inconel 625), nickel, fluorinated 10% CsCl/MgO, and 10% $CsCl/MgF_2$.

The reaction temperature is preferably about 300° C. to about 550° C. and the reaction pressure is preferably about 0 to about 150 psig. Preferably, the reactor effluent is fed to a caustic scrubber or to a distillation column to remove the by-product of HCl to produce an essentially acid-free organic product which, optionally, may undergo further purification.

Example 1: Chlorination of $SbF_5$ by $CHCl_3$

In a 210 ml Hastelloy reactor, 10 g $SbF_5$ (0.046 mol) and 54 g $CHCl_3$ (0.046 mol) were loaded. Then the reactor was heated to 105° C. with agitation and agitated at 105° C. for 12 hours. After that, the reactor was cooled with dry ice, and 100 ml de-ionized water (DI) was injected into the reactor. A gas sample from the vapor space was taken. Then the contents were transferred into a plastic bottle. The aqueous layer was analyzed by ion chromatography (IC). Results are shown in Table 1. IC analysis showed that $CHCl_3$ can efficiently chlorinate $SbF_5$ to $SbCl_5$.

Example 2: Chlorination of $SbF_5$ by Ccl

In a 210 ml Hastelloy reactor, 10 g $SbF_5$ (0.046 mol) and 70 g $CCl_4$ (0.046 mol) were loaded. Then the reactor was heated to 105° C. with agitation and agitated at 105° C. for 12 hours. After that, the reactor was cooled with dry ice, and 100 ml de-ionized water (DI) was injected into the reactor. A gas sample from the vapor space was taken. Then the contents were transferred into a plastic bottle. The aqueous layer was analyzed by ion chromatography (IC). Results are shown in Table 1. IC analysis showed that $CCl_4$ can efficiently chlorinate $SbF_5$ to $SbCl_5$.

Example 3: Chlorination of $Sbf_5$ by 1,1,1,3-Tetrachloropropane (250Fb

In a 210 ml Hastelloy reactor, 10 g $SbF_5$ (0.046 mol) and 115 g 250fb (0.046 mol) were loaded. Then the reactor was heated to 105° C. with agitation and agitated at 105° C. for 12 hours. After that, the reactor was cooled with dry ice, and 100 ml de-ionized water (DI) was injected into the reactor. A gas sample from the vapor space was taken. Then the contents were transferred into a plastic bottle. The aqueous layer was analyzed by ion chromatography (IC). Results are shown in Table 1. IC analysis showed that 250fb can efficiently chlorinate $SbF_5$ to $SbCl_5$.

Example 4: Chlorination of $Sbf_5$ by 2-Chloro-1,1,1,2-Tetrafluoropropane (244Bb In a 210 ml Hastelloy reactor, 10 g $SbF_5$ (0.046 mol) and 70 g 244bb (0.046 mol) were loaded. Then the reactor was heated to 105° C. with agitation and agitated at 105° C. for 12 hours. After that, the reactor was cooled with dry ice, and 100 ml de-ionized water (DI) was injected into the reactor. A gas sample from the vapor space was taken. Then the contents were transferred into a plastic bottle. The aqueous layer was analyzed by ion chromatography (IC). Results are shown in Table 1. IC analysis showed that 244bb can efficiently chlorinate $SbF_5$ to $SbCl_5$.

Example 5: Chlorination of $Sbf_5$ by 2-Chloro-3,3,3-Trifluoropropene (1233Xf

In a 210 ml Hastelloy® reactor, 10 g $SbF_5$ (0.046 mol) and 60 g 1233xf (0.046 mol) were loaded. Then the reactor was heated to 105° C. with agitation and agitated at 105° C. for 12 hours. After that, the reactor was cooled with dry ice, and 100 ml de-ionized water (DI) was injected into the reactor. A gas sample from the vapor space was taken. Then the contents were transferred into a plastic bottle. The aqueous layer was analyzed by ion chromatography (IC). Results are shown in Table 1. IC analysis showed that 1233xf can chlorinate $SbF_5$ to $SbCl_5$.

TABLE 1

| Chlorination Agent | Cl (µg/ml) | F (µg/ml) | F (mol %) | Cl (mol %) |
|---|---|---|---|---|
| $CCl_3H$ | 2125 µg/ml | 115 µg/ml | 9.183 mol % | 90.817 mol % |
| $CCl_4$ | 2057 µg/ml | 2.60 µg/ml | 0.236 mol % | 99.764 mol % |
| 250fb | 208760 µg/ml | 139 µg/ml | 0.125 mol % | 99.875 mol % |
| 244bb | 3450 µg/ml | 21680 µg/ml | 92.151 mol % | 7.849 mol % |
| 1233xf | 985 µg/ml | 14980 µg/ml | 96.600 mol % | 3.400 mol % |

The foregoing description is by way of example only and is not limiting to the scope of the invention.

Embodiments of the present disclosure, for example, in comparison to concepts failing to include one or more of the features disclosed herein, While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A method of chlorinating an antimony fluorohalide catalyst comprising: contacting an antimony fluorohalide catalyst that contains one or more fluorines with a regenerating agent chosen from 2-chloro-3,3,3-trifluoropropene (1233xf), 1,1,1,3-tetrachloropropane (250th), 2-chloro-1,1,1,2-tetrafluoropropane (244bb), and combinations of two or more of 1233xf, 250fb, and 244bb under conditions effective to exchange at least one fluorine in the antimony fluorohalide catalyst with chlorine.

2. The method of claim 1 wherein the regenerating agent comprises 1233xf.

3. The method of claim 1 wherein the regenerating agent comprises 250fb.

4. The method of claim 1 wherein the regenerating agent comprises 244bb.

5. The method of claim 1 wherein the antimony fluorohalide catalyst comprises at least one of (i) $SbF_nX_{5-n}$, wherein n is an integer of 1 to 5, and X is a halogen other than fluorine; and (ii) as $SbFD_mX'_{3-m}$, wherein m is an integer of 1 to 3, and X' is a halogen other than fluorine; or mixtures of (i) and (ii).

6. The method of claim 5 wherein the antimony fluorohalide catalyst comprises $SbF_nX_{5-m}$, wherein n is an integer of 1 to 5, and X is chlorine and the product is a chlorine-containing catalyst.

7. The method of claim 5 wherein the antimony fluorohalide catalyst comprises $SbF_mX'_{3-m}$, wherein m is an integer of 1 to 3, and X' is chlorine.

8. The method of claim 5 wherein the antimony fluorohalide catalyst comprises $SbF_3$.

9. The method of claim 5 wherein the antimony fluorohalide catalyst comprises $SbF_nX_{5-n}$, wherein n is an integer of 1 to 5, and X is chlorine and $SbF_mX'_{3-m}$, wherein m is an integer of 1 to 3, and X' is chlorine.

10. The method of claim 5 wherein the antimony fluorohalide catalyst comprises $SbF_5$, $SbF_4Cl$, $SbF_3Cl_2$, or mixtures thereof.

11. The method of claim 5 wherein the antimony fluorohalide catalyst comprises $SbF_4Cl$ and $SbF_3Cl_2$.

12. The method of claim 1 wherein the contacting occurs at a temperature between about 80° C. and about 120° C.

13. The method of claim 1 wherein the molar ratio of the regenerating agent to the antimony fluorohalide catalyst to the agent is between about 1 to about 5.

14. A method of regenerating and recovering a spent antimony fluorohalide catalyst to produce a chlorinated antimony catalyst comprising:
   (a) treating a spent antimony fluorohalide catalyst comprising
      (i) $SbF_nX_{5-n}$, wherein n is an integer of 1 to 5, and X is a halogen other than fluorine, or
      (ii) $SbF_mX'_{3-m}$, wherein m is an integer of 1 to 3, and X' is a halogen other than fluorine, or mixtures of (i) and (ii),
   with a regenerating agent chosen from 2-chloro-3,3,3-trifluoropropene (1233xf), 1,1,1,3-tetrachloropropane (250th), 2-chloro-1,1,1,2-tetrafluoropropane (244bb), and combinations of two or more of 1233xf, 250fb, and 244bb, under conditions effective to produce a chlorinated antimony catalyst; and (b) recovering the chlorinated antimony catalyst.

15. The method of claim 14 wherein the chlorinated antimony catalyst comprises $SbC_5$.

16. The method of claim 14 wherein the chlorinated antimony catalyst comprises $SbC_3$.

17. The method of claim 14 wherein the contacting occurs at a temperature between about 80° C. and about 120° C.; and the molar ratio of the regenerating agent to the spent antimony is between about 1 to about 5.

18. A composition comprising:
at least one antimony fluorohalide catalyst selected from the group consisting of
(i) $SbF_nX_{5-n}$, wherein n is an integer of 1 to 5, and X is a halogen other than fluorine, and
(ii) $SbF_mX'_{3-m}$, wherein m is an integer of 1 to 3, and X' is a halogen other than fluorine, or mixtures of (i) and (ii); and
at least one compound selected from the group consisting of 2-chloro-3,3,3-trifluoropropene (1233xf), 1,1,1,3-tetrachloropropane (250fb), 2-chloro-1,1,1,2-tetrafluoropropane (HCFC-244bb), and combinations of two or more of 1233xf, 250fb, and 244bb.

\* \* \* \* \*